United States Patent [19]
Salatka et al.

[11] Patent Number: 5,285,896
[45] Date of Patent: Feb. 15, 1994

[54] APPARATUS FOR RECEIVING AND CAPTURING A HYPODERMIC NEEDLE HUB AND CANNULA

[75] Inventors: Robert G. Salatka; William B. Buck, both of Fallbrook; James H. Mitchell, San Diego; William J. Schultz, Encinitas; Leslie Perhacs, Fallbrook, all of Calif.

[73] Assignee: Timely Medical Innovations, Ltd., Carlsbad, Calif.

[21] Appl. No.: 856,631

[22] Filed: Mar. 25, 1992

[51] Int. Cl.⁵ .................................................. B65D 85/24
[52] U.S. Cl. ................................... 206/366; 206/562
[58] Field of Search ............................... 206/363–366, 206/369, 370, 438, 443, 562, 563, 565, 560; 220/908–910

[56] References Cited

U.S. PATENT DOCUMENTS

| | | |
|---|---|---|
| 3,876,067 | 4/1975 | Schwarz . |
| 4,351,434 | 9/1982 | Elisha . |
| 4,488,643 | 12/1984 | Pepper ............................... 206/366 |
| 4,494,652 | 1/1985 | Nelson et al. ....................... 206/366 |
| 4,520,926 | 6/1985 | Nelson ................................ 206/366 |
| 4,883,173 | 11/1989 | Goldman et al. . |
| 4,919,264 | 4/1990 | Shinall . |
| 4,973,315 | 11/1990 | Sincock . |
| 4,984,686 | 1/1991 | Shillington . |
| 5,024,327 | 6/1991 | Shillington . |
| 5,038,929 | 8/1991 | Kubofcik ............................ 206/366 |
| 5,039,004 | 8/1991 | Simpson ............................. 206/366 |
| 5,047,019 | 9/1991 | Sincock . |
| 5,086,922 | 2/1992 | Sagstetter ........................... 206/366 |

Primary Examiner—Jimmy G. Foster
Attorney, Agent, or Firm—Jerry R. Seiler

[57] ABSTRACT

An apparatus for receiving and locking a hypodermic needle hub inserted therein includes a container with a cavity and a top cover with ports. A hypodermic needle cannula and hub may be inserted into each port. Each port has a dimension smaller than the largest cross-sectional dimension of a respective hub. Hub engaging and locking components are secured adjacent the top cover for engaging each hub inserted into a port.

15 Claims, 3 Drawing Sheets

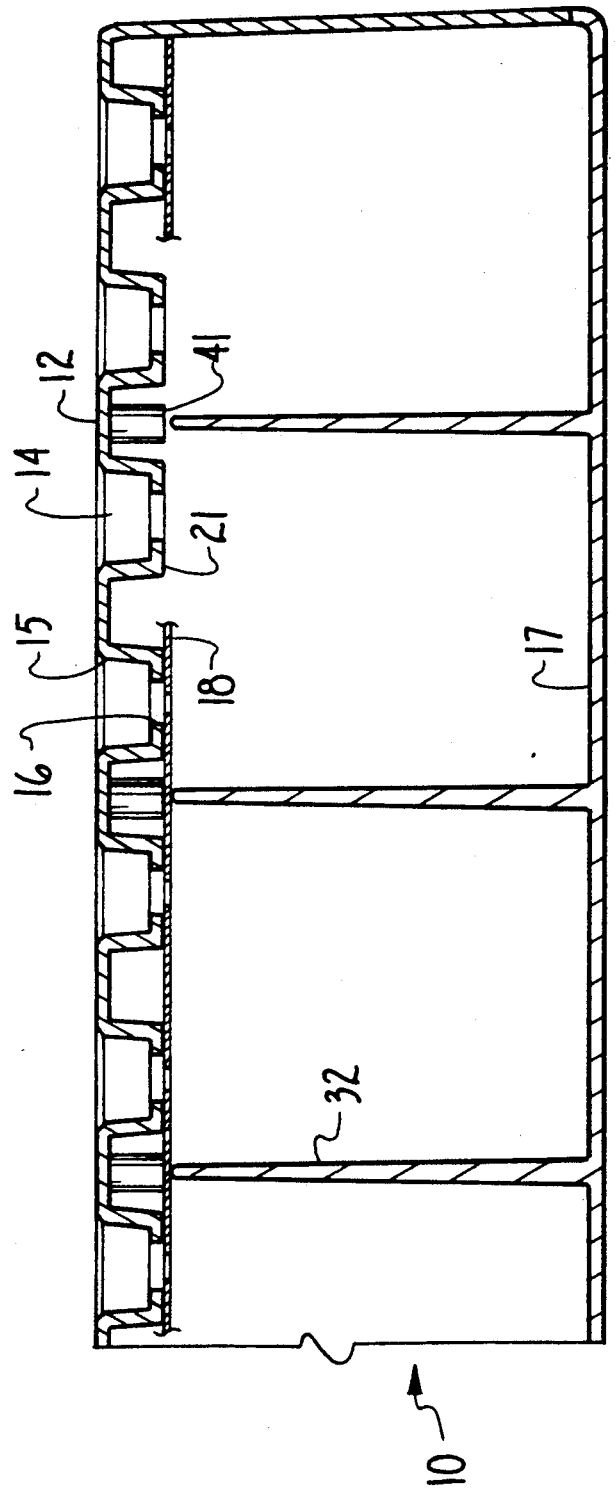
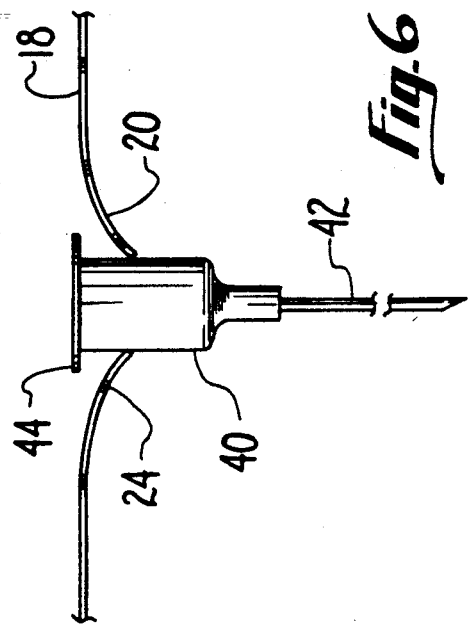
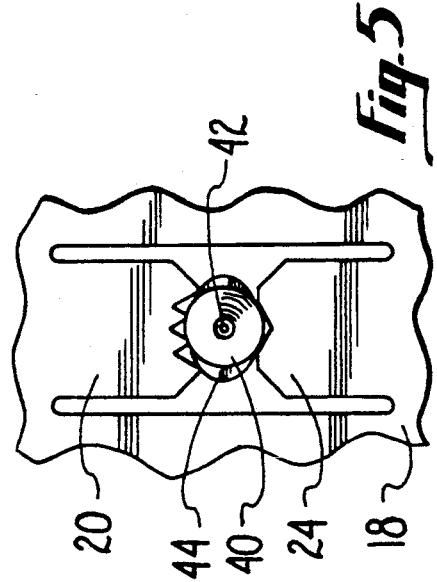

APPARATUS FOR RECEIVING AND CAPTURING A HYPODERMIC NEEDLE HUB AND CANNULA

The effective disposal of hypodermic needles has become especially important with the increased concern for prevention of AIDS and other serious infectious diseases which may be easily transmitted by contact with an infected needle cannula tip. The problem is especially serious in hospitals, clinics, medical offices, and the like where hypodermic needles are used to inject medications and to collect blood samples from patients who are infected with such an illness. Once the needle is retracted from the patient, unless it is discarded so that there is substantially no likelihood or potential for the sharp needle tip to make any contact with the skin of another person, the possibility, if not the likelihood of the serious disease or illness to be unintentionally and accidentally transmitted by such contact may be highly probable.

In many medical and health institutions, needles are discarded in various types of containers, which commonly lack protective means for preventing the sharp needle cannula end from poking a hole through the container, thereby exposing a passerby, or the person who picks up the container to be discarded, to the risk of accidental contact with the sharp needle tip. In other instances, standards and practices for safely discarding such needles, even if conforming to safe practices intended to avoid accidental and inadvertent needle contact with an uninfected person, may not be adequately or carefully followed, thereby causing substantial risks of infection to innocent persons. It is to the elimination of such problems that the apparatus and system of the present invention are directed.

SUMMARY OF THE INVENTION

The present invention is directed to an apparatus for receiving and capturing a hypodermic needle hub having a needle cannula attached to it, in such a way that the captured hub and cannula cannot be retrieved, and are yet held in a protected container interior or cavity in such a manner that accidental contact with the needle tip is all but impossible. The container, in its preferred embodiment, has a plurality of openings which are exposed to the users. The hypodermic needle can be directed into one of the unused openings, needle tip first, whereby the apparatus, which includes needle hub engaging and locking components, automatically lockingly engages and captures the hub. Thereafter, the syringe portion, i.e., the barrel and plunger are pulled away from the hub and needle cannula and discarded The features and components of the apparatus, which provide improved capture of the needle hub and cannula, and substantially prevent removal thereof from the container cavity, will be disclosed hereinafter.

BRIEF DESCRIPTION OF THE DRAWINGS

FIG. 1 is perspective view of a preferred embodiment of the apparatus invention illustrating including means for being removably secured to a wall or the like;

FIG. 2 is a side sectional view of the apparatus;

FIG. 5 is a bottom view and FIG. 6 is a side view both showing a needle hub engaged and locked in the plate.

DETAILED DESCRIPTION OF THE INVENTION

Figure 1:
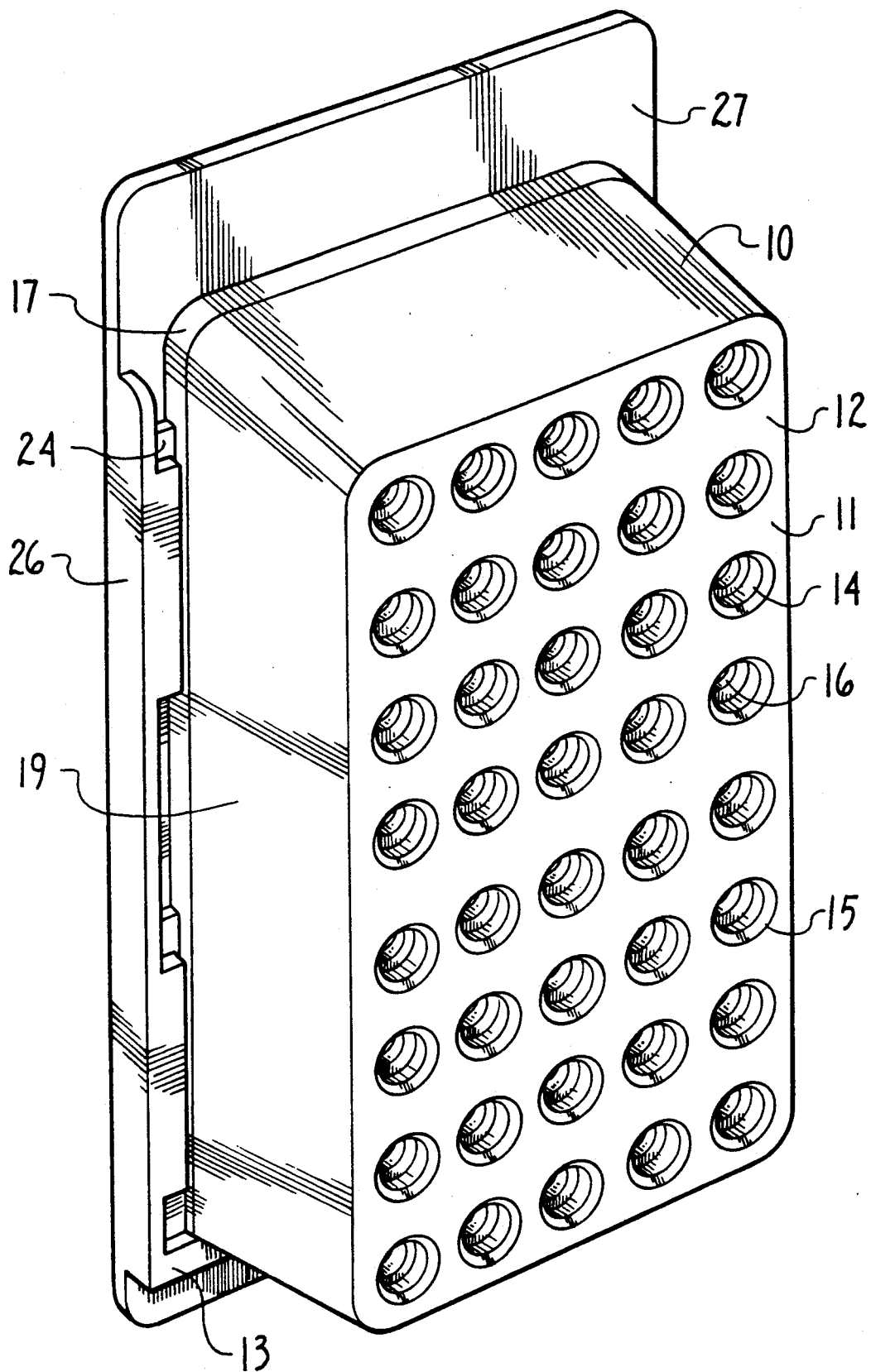

FIGS. 1 and 2 show the container of a preferred embodiment of the apparatus of the invention. The container 10 comprises a top 12 having an outer surface 11 on which are exposed a plurality of ports 14. The ports may be arranged on the outer surface in any desired configuration, and that shown in which the ports are axially aligned in parallel rows may be preferred, but is not critical. However, it will be understood that a configuration which maximizes the number of the ports for a given container size, may be preferred. In addition, preferred configurations of the ports may also provide for ease of visually ascertaining which ports are unused and available for inserting a needle.

The container includes a side 19, which entirely surrounds and defines a cavity in to which the needle cannulae safely extend. Thus, the side must provide a sufficient cavity depth between the top and bottom of the container to allow the capture of needle cannulae of the maximum length normally found or used in the institution in which the apparatus is used. The container also preferably includes a bottom wall which thus encloses the cavity in which the captured needle cannulae will project whereby the container may be readily handled by persons without danger of being injured by any contact with a needle cannula point. The container may be molded to minimize the number of components. However, for assembly purposes, the top and/or bottom are molded as separate components so that the hub engaging plate component can be readily installed during assembly. Thereafter, any separate container components may be glued, fused, or otherwise secured together in final product assembly.

In the embodiment illustrated, the apparatus may also include means for being removably secured on a wall bracket mounted on a wall, door, or similar surface for convenient accessibility. As shown in FIG. 1, a wall plate 27 for being attached to a wall, door, or the like, and having a bracket 26 extending along opposite sides or edges thereof may be conveniently used for removably securing container 10. Flanges 24 formed and extending from bottom plate 17, or other equivalent means for being inserted in the brackets may be used. The brackets may also include a stop member 13 projecting into the bottom of the track or groove between bracket 26 and wall plate surface 27 may be provided for preventing the container inserted in the brackets from gravitationally falling from the holder. Other suitable means may also be used for installing the container in a desirable and readily accessible location for use, and having means for being secured and conveniently removed for disposal.

Figure 3:
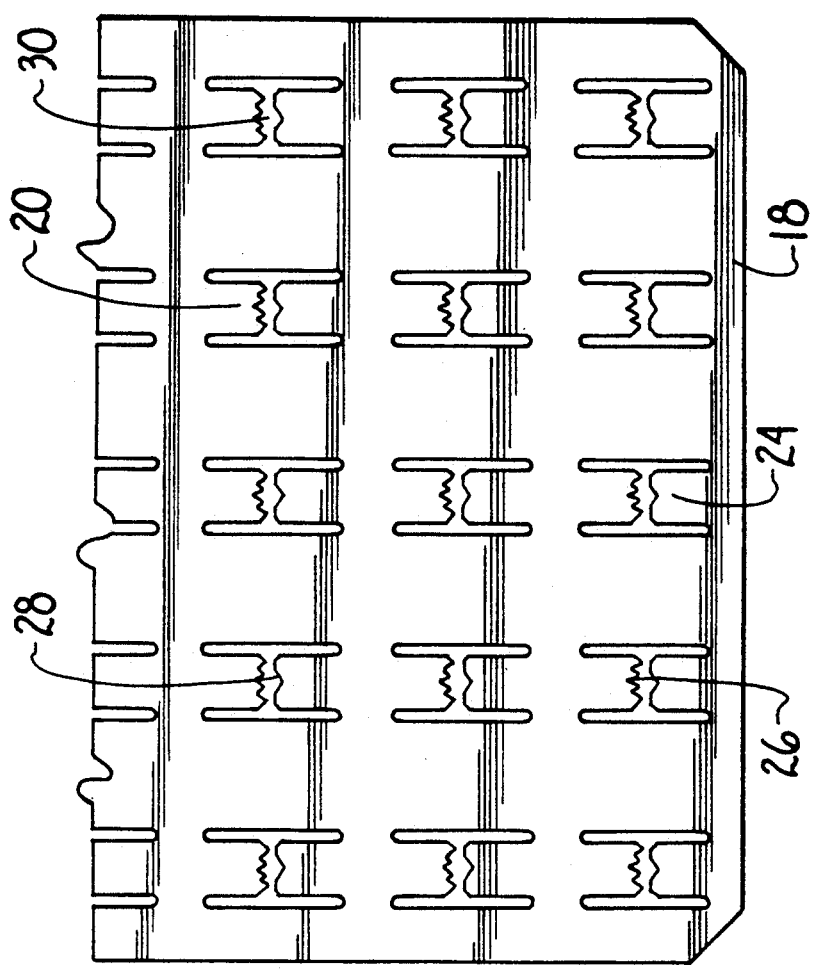
FIG. 3 is a plan view of the needle hub engaging and locking plate of the apparatus illustrating a portion thereof.
Figure 4:
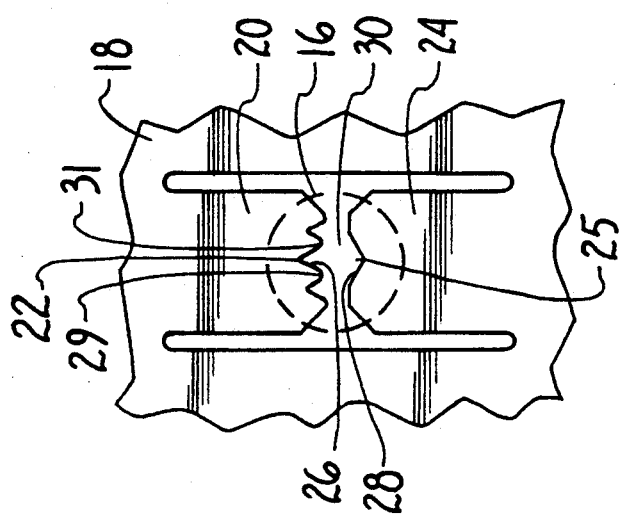
FIG. 4 is an enlarged view of a portion of the plate of FIG. 3 showing the features of the preferred hub engaging and locking components.

FIGS. 3 and 4 illustrate the improved hub engaging, locking and capturing components of the apparatus of the invention. Plate 18 preferably comprises a metal material such as steel, particularly stainless steel or spring steel, which is flexible, and at the same time is memory retaining i.e., spring-like and which tends to return toward its original position after bending, flexing, etc. Plate 18 is provided with a plurality of needle hub engaging and locking components each consisting of a first member 20 having a hub engaging edge 26 and a second member 24 having a hub engaging edge 28.

These first and second members are formed as flexible leafs or fingers, each connected to the plate along one end, and which members are otherwise separated from the plate along both sides and along the hub engaging edges, opposite the plate connection ends, whereby the hub engaging ends are free to be moved. The hub engaging edges of the two members are substantially coplanar and face one another prior to insertion of a needle hub therebetween. The hub engaging edges of the respective members are separated by a space 30 having a maximum dimension that is less than the maximum cross-sectional dimension of the hub to be inserted and engaged by the edges. The plate is preferably made of a stainless steel plate having a substantially uniform thickness of between about 0.009 inch and about 0.011 inch thickness. It has been found that such a thickness lends itself well to meet the requirements of capturing a needle hub inserted between the members. Such metal plate thickness provides for members flexible enough to become spread apart by the needle hub inserted between the hub engaging edges, and yet which are not so flexible as to easily bend to allow the hub to be pulled back out when a hypodermic needle barrel is pulled away from an engaged hub. If the metal plate is thicker than about 0.011 inch, the members will be too stiff and not sufficiently flexible to readily spread the locking components apart by urging the needle hub therebetween. On the other hand, where the plate thickness is less than about 0.009 inch, the components are almost foil-like and are so flexible that they offer insufficient resistance to prevent an engaged needle hub from being pulled back out through the hub engaging edges.

The apparatus is assembled and constructed so that opposite hub engaging edges of the first and second flexible members are centered relative to a port 14 in the top cover. When assembled, as particularly illustrated in FIG. 2, the plate 18 is also secured against the bottom surface 21 of the top cover 12. This may be provided by a number of means, for example, by screwing or bolting the plate to the under surface of the top cover, or by providing a series of small openings in the plate which are registered with nipples or guides extending downwardly from the bottom surface of the top cover having means for holding the plate against the surface. A preferred means is illustrated in FIG. 2, in which the container bottom 17 includes a plurality of supports or ribs 32 which extend from the bottom plate 17 toward the top cover 12, and which ribs are of a length sufficient to hold the plate 18 against the bottom surface 2 of the top cover 12 when the container is assembled. In addition, ribs 32 are preferably spaced and positioned to contact the plate between adjacent hub engaging and locking components whereby movement or flexibility of the hub engaging members to capture a needle hub is not affected. The ribs support the plate in the secured position against the top cover, without bending, forcing or springing the metal plate from its substantially planar condition. In a preferred embodiment shown in FIG. 2 a plurality of bosses 41 may be provided along the underside of top cover 12, to act as additional supports for plate 14 along the opposite side from ribs 32. Thus, the plate 14 is firmly secured between the bosses and ribs.

As shown in FIGS. 3 and 4, the hub engaging edges of the first and second members 20 and 24, respectively, are each provided with an odd number of notches. Surface 28 of member 24 has a single notch 25 substantially centered along edge 28, while edge 26 is provided with three notches, one notch 22 of which is centered along the edge. Thus the two opposite and centered notches 22 and 25 provide a centering aperture in space 30 so that when a needle hub is inserted into the space, it will be guided and become centered in its contact with each of the respective hub engaging surfaces. It is also preferred that, as shown, the two opposite hub engaging surfaces have a different odd number of notches. In the preferred embodiment shown, edge 26 is provided with three notches while edge 28 is provided with a single notch. However, other combinations of odd numbers of facing and opposite coplanar surface notches may be used, whereby one of the surfaces may have five notches and the other one or three notches. In the preferred embodiment, on the three notch hub engaging surface a pair of teeth 29 and 31 as well as surface 28 are provided, one on each side of central notch 22. These teeth are important in engaging and capturing the softer needle hub, commonly made of plastic or aluminum, or other relatively soft material as compared to stainless steel.

When a needle hub is inserted into space 30 between the two opposing hub engaging surfaces 28 and 26, it will be urged to the center of the space because of the opposite and centered notches 22 and 25. As the user continues to force the needle hub into the space, flexible members 20 and 24 bend in the direction the needle hub is urged whereby space 30 becomes enlarged to accommodate the needle hub. At the same time the hub engaging surfaces contact the hub, with teeth 29 and 31 engaging the hub exterior surface. Once the hub is sufficiently engaged by the surfaces, the user pulls the hypodermic needle barrel away from the hub, disengaging it for further disposal. If the barrel features a slip-type needle hub engaging tip, a simple pull in the opposite direction from insertion separates the hypodermic needle components. If the barrel incorporates a Luer Lock in which there is a threaded lock engagement between the needle hub and locking tip of the barrel, the hypodermic needle barrel may be rotated to separate it from the hub. FIGS. 5 and 6 illustrate the locking engagement and capture positions of the needle hub when it is secured between the members as described above. As shown, needle hub 40 is captured between flexible members 20 and 24, which have been bent in the direction in which the needle has been urged for its capture. A portion of needle cannula 42 is also shown.

In another preferred embodiment illustrated in FIGS. 1 and 2, the ports 14 in top cover 12 into which the needle hubs are directed for being captured comprise a first orifice 15 and a second orifice 16 First orifice 15 has a diameter greater than the diameter of second orifice 16. Moreover, the first port diameter is greater than the largest cross-sectional dimension of the needle hub locking tip of the barrel, and the second orifice has a diameter smaller than the largest cross-sectional dimension of the hub. By providing these different relative orifice sizes, the needle hub can be readily passed through the first orifice, but cannot pass through the second orifice. Thus, the smaller orifice 16 opening provides an effective stop and limits the extent to which the hub can be forced into the port and prevents the hub from passing beyond the hub engaging members. Accordingly, the combination of the smaller orifice opening at the interior of the port and adjacent the hub engaging members that provides a substantial improvement of the invention over prior art devices and for effectively capturing a needle hub and cannula. Needle hubs almost universally incorporate a flange 44 at the upper end of the needle hub opposite the cannula, which provides means for threadedly engaging or locking the hub in a hypodermic syringe incorporating locking threads in the locking tip of the barrel. The diameter of the flange normally comprises the greatest cross-sectional dimension of the flange In a hypodermic syringe barrel tip incorporating a slip-type engagement with the needle hub, the locking flange of the hub is exposed on the exterior of the barrel. When the hub having an exposed flange is inserted into the port, it may be urged therein until the flange is stopped from passing through the smaller orifice 16. On the other hand, when inserting hypodermic needle having a barrel provided with a threaded locking tip in which the needle hub flange is threadedly engaged, because the diameter of such a locking tip is greater than the diameter of the smaller orifice, it will stop against the smaller orifice, to prevent further insertion of the hub.

Another preferred and improved feature of the present invention is in the position of plate 18 relative to the smaller orifice 16 as illustrated particularly in FIGS. 2 and 4. With plate 18 being urged to rest against the lower, interior surface 21 of top cover 12, the flexible members 20 and 24 rest against top cover interior surface 21 with the exception of the portion of the members exposed in orifice 16. Because the diameter of orifice 16, represented by the dash lines in FIG. 4, is not great relative to the surface area of either of the flexible members, the movement of the flexible members 20 and 24 from their original coplanar position toward or in the direction of orifice 16 is highly restricted. Preferably, the size of orifice 16 exposes less than 50% of a flexible member surface, and more preferably less than 33%. Such a feature provides a significant safety margin in further preventing retraction or recovery of the needle hub and needle cannula once they have been captured by having been inserted and engaged between the members.

When using the apparatus of the invention, the user simply inserts a hypodermic needle, cannula point first, into one of the ports on the top cover. As the user continues to insert the hypodermic needle into the port, the hub will become engaged between the facing hub engaging surfaces. Urging of the hypodermic needle is continued until the locking flange of the hub contacts the small inner port orifice and can no longer be forced further into the port or until the enlarged locking tip of a threaded (Luer lock) type of barrel is stopped by the small orifice. At that time, the hub and needle cannula are fully engaged and captured, and the user then simply pulls the hypodermic needle syringe away from the hub. The apparatus may be used until all of the ports are filled, and thereafter discarded. These as well as other features and advantages within the scope of the invention will be evident to those skilled in the art.

We claim:

1. Apparatus for receiving and locking a hypodermic needle hub inserted therein comprising:
   a container having a cavity and a top cover having a plurality of ports for inserting a hypodermic needle cannula and hub therein, each of such ports having a dimension smaller than the largest cross-sectional dimension of said hub, whereby said hub may not entirely pass therethrough, and
   a plurality of hub engaging and locking components each component comprising first and second flexible and memory retaining members, each member having a hub engaging edge, wherein said hub engaging edge of each of said first and second members has a notch substantially centered along said hub engaging edge and wherein said notches are substantially opposite one another, said hub engaging edges being substantially coplanar and facing one another and spaced apart a first distance less than a cross-sectional dimension of said hub to be engaged therebetween and capable of being spread apart to a second distance, greater than said first distance by urging said hub therebetween whereby said hub is engaged and locked therebetween, each of said hub engaging and locking components being aligned relative to a different one of said ports, whereby said edges are exposed in said ports, with said space between the facing hub engaging edges substantially centered relative to a port,
   said components being secured adjacent to said top cover and proximate thereto whereby movement of said firs and second member in a direction toward said top cover is limited by abutment of said members thereagainst.

2. Apparatus of claim 1 wherein said notches are substantially centered relative to the port in which they are exposed.

3. Apparatus of claim 1 wherein said hub engaging edge of said first member comprises a plurality of notches therealong, wherein a first one of said notches is substantially centered along said hub engaging edge of said first member relative to said port, and wherein said hub engaging edge of said second member has a single notch substantially centered along said hub engaging edge of said second member and substantially centered relative to said port, and facing said first one of said plurality of notches of said hub engaging edge of said first member.

4. Apparatus of claim 3 wherein said hub engaging edge of said first member includes a tooth projecting therefrom between each of said plurality of notches.

5. Apparatus of claim 4 wherein said first member comprises an odd number of said plurality of notches and an even number of teeth along said hub engaging edge.

6. Apparatus of claim 5 wherein said hub engaging surface of said second member has a tooth projecting from said surface on opposite sides of said single notch.

7. Apparatus of claim 6 wherein the teeth of said first and second members are substantially coplanar and extend into a space between said hub engaging surfaces.

8. Apparatus of claim 1 wherein said top cover comprises a top surface exposed outside of said container and a bottom surface facing the interior of said container, wherein each of said ports comprises a first orifice exposed on said top surface and a second orifice exposed on said bottom surface and wherein the diameter of said first orifice is greater than the largest cross-sectional dimension of said needle hub and wherein the diameter of said second orifice is smaller than the largest cross sectional dimension of said needle hub.

9. Apparatus of claim 1 comprising a substantially planar plate having said hub engaging and locking components formed thereon.

10. Apparatus of claim 9 wherein said plurality of hub engaging and locking components are aligned along one or more axes.

11. Apparatus of claim 9 wherein said hub engaging and locking components are aligned along two or more parallel rows.

12. Apparatus of claim 11 wherein said container includes a plurality of support members abutting said planar plate between said rows of said components.

13. Apparatus of claim 9 wherein said plate comprises a memory retaining metal plate having a substantially uniform thickness of between about 0.009 inch and about 0.011 inch.

14. Apparatus of claim 9 wherein said plate comprises stainless steel.

15. Apparatus of claim 9 wherein said plate comprises spring steel.

* * * * *